United States Patent
Gundersen

(10) Patent No.: US 11,493,375 B2
(45) Date of Patent: Nov. 8, 2022

(54) SEPARATION TYPE MULTIPHASE FLOWMETER WITH SEPARATE FLOW METERING DEVICES WITH DIFFERENT CROSS-SECTIONAL AREAS

(71) Applicant: FMC Kongsberg Subsea AS, Kongsberg (NO)

(72) Inventor: Kenneth Gundersen, Bryne (NO)

( * ) Notice: Subject to any disclaimer, the term of this patent is extended or adjusted under 35 U.S.C. 154(b) by 165 days.

(21) Appl. No.: 16/643,497

(22) PCT Filed: Aug. 31, 2018

(86) PCT No.: PCT/EP2018/073472
§ 371 (c)(1),
(2) Date: Feb. 28, 2020

(87) PCT Pub. No.: WO2019/043160
PCT Pub. Date: Mar. 7, 2019

(65) Prior Publication Data
US 2020/0209035 A1    Jul. 2, 2020

(30) Foreign Application Priority Data
Aug. 31, 2017 (NO) .................................. 20171416

(51) Int. Cl.
*G01F 7/00*    (2006.01)
*G01F 1/66*    (2022.01)
(Continued)

(52) U.S. Cl.
CPC ................ *G01F 7/00* (2013.01); *G01F 1/662* (2013.01); *G01F 1/74* (2013.01); *G01F 15/08* (2013.01);
(Continued)

(58) Field of Classification Search
None
See application file for complete search history.

(56) References Cited

U.S. PATENT DOCUMENTS 5,048,348 A    9/1991   Durrett et al.
5,390,547 A *  2/1995   Liu .......................... G01F 1/74
                                                    73/200

(Continued)

FOREIGN PATENT DOCUMENTS

EP    1 899 687 B1      9/2010
GB    2 307 300 A       5/1997
WO    WO 2006/121480 A2   11/2006

OTHER PUBLICATIONS

Corneliussen et al., Handbook of Multiphase Flow Metering, Rev. 2, Mar. 2005 (ISBN 82-91341-89-3), pp. 37-39.

*Primary Examiner* — Harshad R Patel

(57) ABSTRACT

A separation type multiphase flow meter apparatus (10) comprising a separation module (18) arranged to at least partially separate a multiphase stream comprising water, hydrocarbon liquid and hydrocarbon gas into a first sub-stream comprising a gas fraction and a second sub-stream comprising a liquid fraction. The apparatus comprises a first metering device (16) for measuring the flow rate of the first sub-stream, and a second metering device (17) for measuring the phase fraction and the flow rate of the second sub-stream, wherein the second metering device is arranged to measure the water-in-liquid ratio (WLR) of the second sub-stream, wherein the apparatus is arranged to use the WLR measured by the second metering device as a measure also for the WLR of the first sub-stream, and wherein the cross-sectional flow area of the first metering device is larger than the cross-sectional flow area of the second metering device.

10 Claims, 2 Drawing Sheets

(51) Int. Cl.
*G01F 1/74* (2006.01)
*G01F 15/08* (2006.01)
*G01N 22/04* (2006.01)
*G01N 33/28* (2006.01)

(52) U.S. Cl.
CPC ......... *G01N 22/04* (2013.01); *G01N 33/2823* (2013.01); *G01N 33/2847* (2013.01)

(56) References Cited

U.S. PATENT DOCUMENTS

| | | |
|---|---|---|
| 6,532,826 B1 | 3/2003 | Dou |
| 6,802,204 B1 * | 10/2004 | Torkildsen .............. G01F 15/08 73/61.44 |
| 7,661,302 B2 * | 2/2010 | Gysling ................. G01N 33/26 73/200 |
| 9,114,332 B1 * | 8/2015 | Liu .................... B01D 17/0208 |
| 2007/0006640 A1 | 1/2007 | Gysling |
| 2007/0006727 A1 | 1/2007 | Gysling |
| 2014/0007696 A1 * | 1/2014 | Al-Hadhrami ............ G01F 1/74 73/861.04 |

* cited by examiner

SEPARATION TYPE MULTIPHASE FLOWMETER WITH SEPARATE FLOW METERING DEVICES WITH DIFFERENT CROSS-SECTIONAL AREAS

FIELD OF THE INVENTION

The present invention relates to a separation type multiphase flow meter apparatus comprising a separation module arranged to at least partially separate a multiphase stream comprising water, hydrocarbon liquid and hydrocarbon gas into a first sub-stream comprising a gas fraction and a second sub-stream comprising a liquid fraction.

BACKGROUND

The present invention relates to a hydrocarbon multiphase flow meter (MPFM), i.e. an apparatus for measuring the individual flow rates of hydrocarbon liquid, water and hydrocarbon gas in a multiphase hydrocarbon flow. In particular, the present invention relates to a separation type MPFM.

In this specification the terms "oil" and "gas" will be used to denote hydrocarbons which are in the liquid and gaseous state, respectively, at the prevailing temperature and pressure conditions, and the term "phase" will be used to denote one constituent of gas, oil and water in a mixture of any number of the three.

Separation type MPFMs are discussed, for example, in section 7.1.2 of HANDBOOK OF MULTIPHASE FLOW METERING, Rev. 2, March 2005 (ISBN-82-91341-89-3). In a separation type MPFM, a complete or partial separation of the multiphase hydrocarbon flow is performed in a separation stage or module, followed by in-line measurements of each of the three phases. In a partial separation type MPFM, which is discussed in section 7.1.2.2 of the above-mentioned HANDBOOK, only a part of the gas in the multiphase flow is separated into a secondary, gas measurement loop, while the rest of the flow is guided through a main, liquid measurement loop. Since the separation is only partial, one must expect some liquid (oil and water) to travel with the gas through the secondary measurement loop, which then calls for a wet gas meter to be used in this loop. The multiphase flow going through the main measurement loop will have a reduced gas-volume-fraction, GVF, and the individual flow rates of the phases in the main measurement loop can thereby be measured using a conventional multi-phase meter.

However, this configuration is not suited for subsea use. In particular, use of conventional multi-phase and wetgas meters in the measurement loops requires the separation stage to be efficient enough to ensure a GVF in the respective measurement loop to be above and below, respectively, a GVF threshold, e.g. 95%. This, in turn, requires an active regulation of the separation module, which normally is not an option in subsea applications. Also, the configuration is not suitable when there are slugs in the hydrocarbon flow, as is common in subsea applications, since the required GVF operational range required by conventional multi-phase and wetgas meters cannot be guaranteed under such circumstances.

In summary, in order to guarantee the GVF operational range required by a conventional multi-phase meter, the configuration suggested in section 7.1.2.2 of the above-mentioned HANDBOOK may, in many applications, require a large, actively regulated separation module of a type which is not an option in subsea applications.

With the abovementioned challenges and known solutions in mind, the present invention seeks to bring forward a simple separation type MPFM which is especially suited for subsea use.

SUMMARY OF THE INVENTION

According to one aspect, the invention relates to a separation type multiphase flow meter apparatus comprising a separation module arranged to at least partially separate a multiphase stream comprising water, hydrocarbon liquid and hydrocarbon gas into a first sub-stream comprising a gas fraction and a second sub-stream comprising a liquid fraction. The apparatus further comprises a first metering device for measuring the flow rate of the first sub-stream; and a second metering device for measuring the phase fraction and the flow rate of the second sub-stream, wherein the second metering device is arranged to measure the water-in-liquid ratio (WLR) of the second sub-stream, wherein the apparatus is arranged to use the WLR measured by the second metering device as a measure also for the WLR of the first sub-stream, and wherein the cross-sectional flow area of the first metering device is larger than the cross-sectional flow area of the second metering device.

The first sub-stream may comprise a gas fraction and a liquid fraction, and the first metering device may be arranged to measure the gas and liquid flow rates of the first sub-stream.

In the first sub-stream the gas fraction may be larger than the liquid fraction, i.e. the first sub-stream may comprise for the most part a gas fraction, and in the second sub-stream the liquid fraction may be larger than the gas fraction, i.e. the second sub-stream may comprise for the most part a liquid fraction.

The first and second metering devices may be arranged to acquire multiphase and wet gas measurements within the gas-volume-fraction (GVF) range of 0-100%.

The first metering device may be a dual-phase meter, e.g. configured to measure gas and liquid mass and volume flow rates, and the second metering device may advantageously be a multiphase meter, e.g. an electromagnetic, microwave type multiphase meter.

The separation module may comprise:

an inlet conduit configured to receive, at an inlet, the multiphase stream;

a first measuring or separation conduit configured to receive, from the inlet conduit, said first sub-stream, in which first measuring conduit the first metering device is arranged;

a second measuring or separation conduit configured to receive, from the inlet conduit, said second sub-stream, in which second measuring conduit the second metering device is arranged; and an outlet conduit configured to receive the first sub-stream from the first measuring conduit and the second sub-stream from the second measuring conduit, and to output, at an outlet, the re-joined multiphase stream, wherein the first measuring conduit extends orthogonally or substantially orthogonally from the inlet conduit; and wherein, when the apparatus is in operation, the inlet conduit is configured to have a horizontal or substantially horizontal orientation and the first measuring conduit is configured to extend vertically upwardly or substantially vertically upwardly from the inlet conduit allowing the first sub-stream to be conveyed vertically upwardly or substantially vertically upwardly in the first measuring conduit, and allowing the second sub-stream to be conveyed horizontally or substantially horizontally in the inlet conduit downstream of the first measuring conduit.

This will provide a partial separation type multiphase meter apparatus having a simple and robust design which does not require active control of the separation process. Advantageously, both the first and second metering devices are configured to handle a GVF within the range of 0%≤GVF≤100%. This will allow the apparatus to handle situation and be fully functional also when there is limited or no gas-liquid separation, e.g. when slugs occur in the system.

The design will also allow the separation module to be made from standard subsea piping elements, which may be advantageous since such elements are well known and qualified for subsea use and development.

The second measuring conduit may extend orthogonally or substantially orthogonally from the inlet conduit coplanar with and downstream of the first measuring conduit.

The outlet conduit may be arranged in parallel with the inlet conduit.

Generally, a multiphase meter has limitations when it comes to scalability. If the cross-sectional flow area of the multiphase meter is made large to accommodate a large flow, the transmitted signals from the multiphase meter, which, for example, can be electromagnetic signals or gamma photons of lower energy, may deteriorate and/or attenuate. However, the apparatus according to the present invention allows a small-diameter multiphase meter to be used in the second measuring conduit, while scaling of the flow can be handled by increasing the diameter of the dual-phase meter, which, by virtue of utilising the WLR signal from the multiphase meter, can provide accurate flow rate values for the sub-stream in the first measuring conduit.

Scalability can particularly be a challenge when the multiphase flow contains high salinity water (for example water having a salinity weight percent above 13%), and the present invention will be particularly relevant in such situations since even moderate size meters (e.g. having a bore diameter of 4") can be prohibited by high signal attenuation caused by high salinity water. However, by having a small-diameter multiphase meter on the second measuring conduit, adequate signal transmission, and thereby adequate WLR measurement, can be achieved for high salinity water applications.

The diameter of the cross-sectional flow area of the first and second metering devices may for example be 5" and 3", respectively.

For the intention of making a working multiphase meter apparatus for a multiphase flow comprising high salinity water, the degree of partial phase splitting is not strictly relevant since it is the reduced inner diameter in the second measuring device that is the key element for this. Partial separation multiphase meter apparatuses have previously not been aimed at handling the scalability challenge associated with multiphase flows comprising high salinity water.

In addition to scalability, a second advantage achieved of the present invention is that it allows for potentially more accurate measurement of liquid properties (e.g. WLR and water salinity) by the multiphase meter in the second measuring conduit since less gas will be present there. This makes the current invention relevant not only for high salinity water wells, but also for any application and/or well where a high gas fraction makes it challenging to achieve sufficiently accurate measurement of WLR and water salinity using a single standard in-line multiphase meter. The present invention is also relevant in situations where it is not practical to install a full-blown separation device capable of achieving the separation quality necessary for existing partial separation multiphase meters.

According to one aspect of the invention, the separation module may comprise an inlet conduit, an outlet conduit and first and second measuring or separation conduits arranged side by side between and in fluid communication with the inlet and outlet conduits, wherein the first metering device is arranged in the first measuring conduit, which forms a conduit path for the first sub-stream, and wherein the second metering device is arranged in the second measuring conduit, which forms a conduit path for the second sub-stream.

When the separation module is in use, the inlet conduit and the outlet conduit may have a horizontal or substantially horizontal orientation, and the first and second measuring conduits may have a vertical or substantially vertical orientation.

The conduits of the separation module may be made from subsea piping elements, e.g. subsea grade piping or ordinary subsea piping elements. As stated above, using such elements may be advantageous since they are well known and qualified for subsea use and development.

DESCRIPTION OF THE DRAWINGS

Following drawing is appended to facilitate the understanding of the invention.

Figure 1:
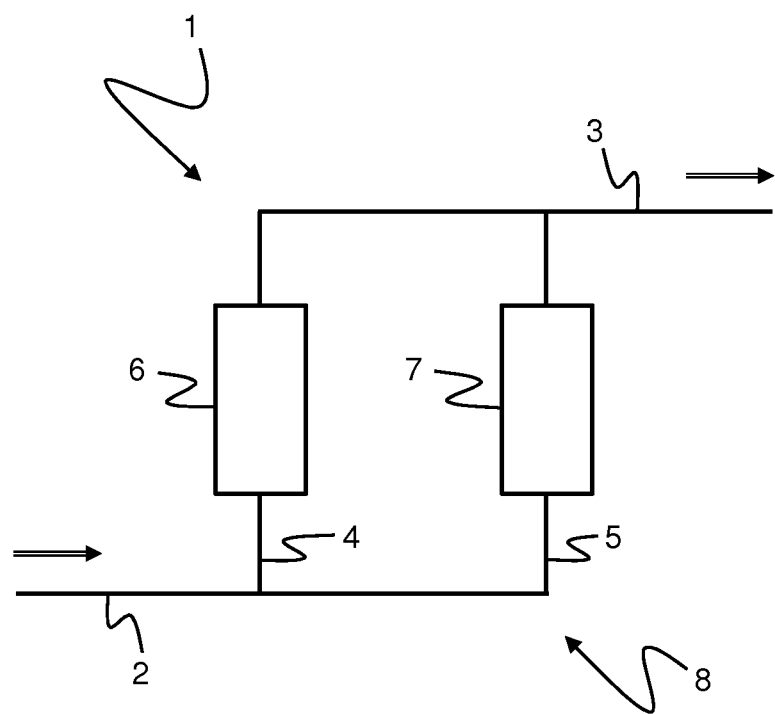
FIG. 1 shows a separation type multiphase flow meter apparatus according to one embodiment of the invention.

It should be understood, however, that the drawings are not intended to limit the invention to the subject-matter depicted in the drawings.

In the drawings, like reference numerals have been used to indicate common parts, elements or features unless otherwise explicitly stated or implicitly understood by the context.

DETAILED DESCRIPTION OF THE INVENTION

FIG. 1 shows an embodiment of a separation type multiphase flow meter apparatus 1 according to the invention.

The apparatus 1 comprises an inlet conduit 2 and an outlet conduit 3. The apparatus 1 further comprises first and second measuring or separation conduits 4, 5 being arranged side by side between and in fluid communication with the inlet and outlet conduits 2, 3, thus allowing parallel fluid flows therein. Consequently, the first measuring conduit 4 forms a first conduit path of the apparatus 1 and the second measuring conduit 5 forms a second conduit path of the apparatus 1, which first and second conduit paths run side by side in a parallel, i.e. non-serial, configuration.

In operation, a multiphase fluid will enter the apparatus 1 via inlet conduit 2 and be split into two sub-streams in measuring conduits 4 and 5, which sub-streams will be re-joined in outlet conduit 3 and exit the apparatus 1 via this conduit, as is indicated by the arrows in FIG. 1. Conduits 2-5 form a separation module 8 of the apparatus 1 arranged to at least partially separate the multiphase stream comprising water, hydrocarbon liquid and hydrocarbon gas into a first sub-stream comprising a gas fraction and a second sub-stream comprising a liquid fraction.

In the embodiment shown in FIG. 1, the input and output conduits 2, 3 are substantially horizontal and the measuring conduits 4, 5 are substantially vertical. The conduits 2-5 may advantageously be made from ordinary or standard subsea piping, e.g. duplex pipes, providing a simple, rugged separation module design suitable for subsea applications.

The first measuring conduit 4 is arranged upstream of the second measuring conduit 5 and due to the higher impulse of liquids than gases, and the fact that liquid will tend to flow at the bottom of inlet conduit 2, the liquid loading in measuring conduit 5 will be higher than in measuring conduit 4. In other words, the GVF of the sub-stream flowing through conduit 4 will normally be higher than the GVF of the sub-stream flowing through conduit 5.

Figure 2:
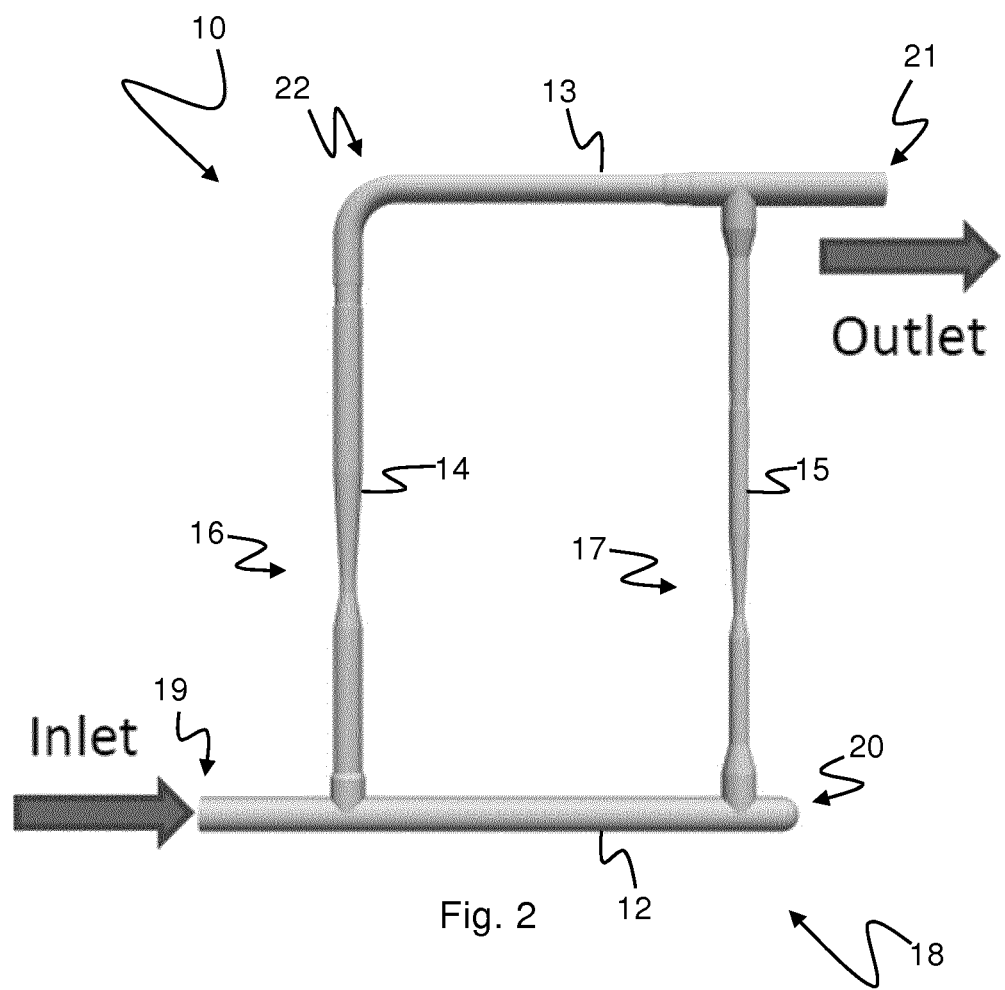
FIG. 2 shows a separation type multiphase flow meter apparatus according to a second embodiment of the invention.

FIG. 2 shows an embodiment of a multiphase flow meter apparatus 10 according to a second embodiment of the invention.

The apparatus 10 comprises a linear or substantially linear first conduit 12. The first conduit 12 comprises an inlet 19 at one end. At a second end 20 opposite the inlet 19, the first conduit 12 is capped.

The apparatus 10 also comprises a linear or substantially linear second conduit 13 which comprises an outlet 21 at one end. The second conduit 13 is arranged parallel or substantially parallel to the first conduit 12.

The apparatus 10 further comprises a linear or substantially linear third conduit 14 which extends orthogonally or substantially orthogonally from the first conduit 12 between the inlet 19 and the capped end 20. The third conduit 14 is connected to the second conduit 13 at a second end 22 of the second conduit 13 opposite the outlet 21. The apparatus 10 also comprises a linear or substantially linear fourth conduit 15 which extends orthogonally or substantially orthogonally from the first conduit 12 between the second conduit 14 and the capped end 20. The fourth conduit 15 is connected to the second conduit 13 between the second end 22 and the outlet 21.

The first 12, second 13, third 14 and fourth 15 conduits are co-planar or substantially co-planar, and when the apparatus 10 is in operation the plane in which the conduits 13-15 are arranged is vertically or substantially vertically orientated so that the first 12 and second 13 conduits assume a horizontal or substantially horizontal orientation, and the third 14 and fourth 15 conduits assume a vertical or substantially vertical orientation.

In operation, a multiphase fluid will enter the apparatus 10 via the inlet 19. At the third conduit 14, the horizontally flowing multiphase fluid stream will be split into a first sub-stream which will flow vertically in conduit 14 and into a second sub-stream which will continue to flow horizontally in conduit 12 and eventually enter conduit 15. Due to the horizontal configuration of conduit 12 and the vertical configuration of conduit 14, and due to the higher impulse of liquids than gases and the fact that liquid will tend to flow at the bottom of conduit 12, conduit 14 will sample more gas than conduit 15 and, consequently, the liquid loading in conduit 15 will be higher than in conduit 14. In other words, the GVF of the sub-stream flowing through conduit 14 will normally be higher than the GVF of the sub-stream flowing through conduit 15.

Conduits 13 and 15 may in general have any orientation, but by arranging conduit 13 and 15 parallel to conduit 12 and 14, respectively, a compact design of the apparatus can be achieved.

Consequently, in FIG. 2 conduits 12-15 form a separation module 18 of the apparatus 10 arranged to at least partially separate the multiphase stream into a first sub-stream comprising a gas fraction and a second sub-stream comprising a liquid fraction. The first conduit 12 will act as an inlet conduit of the separation module 18. Conduit 14 will act as a first measuring or separation conduit forming a first conduit path of the separation module 18 of the apparatus 10, and conduit 15 will act as a second measuring or separation conduit forming a second conduit path of the separation module 18, which first and second conduit paths run side by side in a parallel, i.e. non-serial, configuration. The sub-streams will be re-joined in conduit 13 and exit the apparatus 10 via outlet 21. Consequently, conduit 13 will act as an outlet conduit of the separation module 18.

In the following, reference will be made to both FIG. 1 and FIG. 2.

A metering device 6, 7; 16, 17 being able to acquire multiphase and wet gas measurements within the full GVF range of 0-100% is arranged in each measuring conduit 4, 5; 14, 15. By choosing such metering devices, the phase splitting in the separation module need not be perfect and the unpredictability associated with subsea applications as to GVF:s in the sub-streams can be handled.

The first phase metering device 6; 16 may for example be a dual-phase meter, and the second phase metering device 7; 17 may be a full range electromagnetic, microwave type multiphase meter. Due to the relatively low GVF of the sub-stream flowing through measuring conduit 5; 15 during normal operation conditions, a relatively accurate water-in-liquid ratio (WLR) measurement for the low GVF sub-stream can be achieved.

For dual-phase meter 6; 16 WLR measuring is not necessary since dual-phase meter 6; 16 only measures gas and liquid rates and can rely on WLR measurements from multiphase meter 7; 17. Relevant values, e.g. gamma densitometer and differential pressure values of dual-phase meter 6; 16, are transmitted to and processed by the electronics in multiphase meter 7; 17.

According to one aspect of the invention, a rough phase splitting module can be achieved using standard piping or similar that is uncontroversial to use subsea. At the same time, the metering device 6, 7; 16, 17 in each measuring conduit 4, 5; 14, 15 is capable of handling the imperfect phase splitting, but at the same time exploits that better WLR and liquid rate measurements can be achieved in the sub-stream flowing through measuring conduit 5; 15.

As discussed above, the WLR is assumed to be equal in both sub-streams, but if this in some rare case is questionable, a mixing element (not shown in FIG. 1 and FIG. 2) may be arranged upstream of the measuring conduits 4, 5; 14, 15.

The apparatus 1; 10 will provide a compact design and the proposed solution will be shorter in length than a standard single conduit in-line solution, and only marginally wider.

It should be noted that the apparatus 1; 10 according to the invention will still function as an MPFM even if the splitting module is not capable of phase-splitting the main flow and the GVF becomes equal in both sub-flows, as may sometimes happen in subsea applications. The performance of the apparatus 1; 10 will then be comparable to that of a multiphase meter operating at the same GVF.

Another problem associated with subsea application is scalability. Increasing flows require that larger pipe dimensions in the phase meters are used. For an electromagnetic, microwave type multiphase meter this may be a problem since this means that the microwave antennas will become positioned further apart, thus resulting in a weaker signal. This problem is amplified if the water phase has a high salinity.

It is known to alleviate this problem by substituting a single electromagnetic, microwave type multiphase meter for a plurality of smaller diameter meters arranged in parallel.

However, the apparatus according to the present invention allows an alternative solution. In particular, the apparatus 1 allows a small-diameter electromagnetic, microwave type multiphase meter 7 to be maintained, while scaling of the flow is handled by increasing the diameter of the dual-phase meter 6. By assuming that the WLR is the same in both conduits 4 and 5, a dual-phase meter 6, which is not affected by scaling problems, can be used in conduit 4. Consequently, according to one embodiment of the apparatus, a dual-phase meter 6 is used in conduit 4, an electromagnetic, microwave type multiphase meter 7 is used in conduit 5, and the cross-sectional area of dual-phase meter 6 is arranged to be larger than the cross-sectional area of electromagnetic, microwave type multiphase meter 7. For example, the multiphase meter 7 can typically be a 2 inch diameter meter and the dual-phase meter 6 can be freely sized according to the flow requirements.

In the embodiment shown in FIG. 2, the minimum cross-sectional flow area of the first separation conduit 14 and the first metering device 16 arranged therein is larger than the minimum cross-sectional flow area of the second separation conduit 15 and the second metering device 17 arranged therein. In this embodiment, the diameter of the cross-sectional flow area of the first and second metering devices 16, 17 is 5" and 3", respectively.

In the preceding description, various aspects of the apparatus according to the invention have been described with reference to the illustrative embodiment. For purposes of explanation, specific numbers, systems and configurations were set forth in order to provide a thorough understanding of the apparatus and its workings. However, this description is not intended to be construed in a limiting sense. Various modifications and variations of the illustrative embodiment, as well as other embodiments of the apparatus, which are apparent to person skilled in the art to which the disclosed subject-matter pertains, are deemed to lie within the scope of the present invention as defined by the following claims.

The invention claimed is:

1. A separation type multiphase flow meter apparatus comprising:
   a separation module arranged to at least partially separate a multiphase stream comprising water, hydrocarbon liquid and hydrocarbon gas into a first sub-stream comprising a gas fraction and a second sub-stream comprising a liquid fraction;
   a first metering device for measuring a flow rate of the first sub-stream; and
   a second metering device for measuring a phase fraction and a flow rate of the second sub-stream;
   wherein the second metering device is arranged to measure a water-in-liquid ratio (WLR) of the second sub-stream;
   wherein the apparatus is arranged to use the water-in-liquid ratio (WLR) measured by the second metering device as a measure for a water-in-liquid ratio (WLR) of the first sub-stream;
   wherein a cross-sectional flow area of the first metering device is larger than a cross-sectional flow area of the second metering device; and
   wherein the separation module comprises:
      an inlet conduit having an inlet configured to receive the multiphase stream;
      a first measuring conduit configured to receive from the inlet conduit said first sub-stream, the first metering device being arranged in the first measuring conduit;
      a second measuring conduit configured to receive from the inlet conduit said second sub-stream, the second metering device being arranged in the second measuring conduit; and
      an outlet conduit configured to receive the first sub-stream from the first measuring conduit and the second sub-stream from the second measuring conduit and to output at an outlet the re-joined multiphase stream,
      wherein the first measuring conduit extends orthogonally from the inlet conduit and wherein, when the apparatus is in operation, the inlet conduit is configured to have a horizontal orientation and the first measuring conduit is configured to extend vertically upwardly from the inlet conduit, thereby allowing the first sub-stream to be conveyed vertically upwardly in the first measuring conduit and the second sub-stream to be conveyed horizontally in the inlet conduit downstream of the first measuring conduit.

2. The apparatus according to claim 1, wherein the first sub-stream comprises a gas fraction and a liquid fraction and the first metering device is arranged to measure the gas and liquid flow rates of the first sub-stream.

3. The apparatus according to claim 1, wherein the first and second metering devices are arranged to acquire multiphase and wet gas measurements over an entire gas-volume-fraction (GVF) range of 0-100%.

4. The apparatus according to claim 1, wherein the first metering device is a dual-phase meter and the second metering device is an electromagnetic, microwave type multiphase meter.

5. The apparatus according to claim 1, wherein the second measuring conduit extends orthogonally from the inlet conduit and co-planar with and downstream of the first measuring conduit.

6. The apparatus according to claim 5, wherein the outlet conduit is arranged in parallel with the inlet conduit.

7. The apparatus according to claim 1, wherein the inlet conduit, the outlet conduit, the first measuring conduit and the second measuring conduit are made from subsea piping elements.

8. The apparatus according to claim 1, wherein the separation module comprises an inlet conduit, an outlet conduit and first and second measuring conduits arranged side by side between and in fluid communication with the inlet and outlet conduits, wherein the first metering device is arranged in the first measuring conduit, which forms a conduit path for the first sub-stream, and wherein the second metering device is arranged in the second measuring conduit, which forms a conduit path for the second sub-stream.

9. The apparatus according to claim 8, wherein the inlet conduit and the outlet conduit have a generally horizontal orientation, and wherein the first and second measuring conduits have a generally vertical orientation when the apparatus is in use.

10. The apparatus according to claim 8, wherein the inlet and outlet conduits and the first and second measuring conduits are made from subsea piping elements.

* * * * *